United States Patent [19]

Keyes

[11] Patent Number: 4,716,116
[45] Date of Patent: * Dec. 29, 1987

[54] PROTEIN MODIFICATION TO PROVIDE ENZYME ACTIVITY

[75] Inventor: Melvin H. Keyes, Sylvania, Ohio

[73] Assignee: Owens-Illinois Glass Container Inc., Toledo, Ohio

[*] Notice: The portion of the term of this patent subsequent to Sep. 2, 2003 has been disclaimed.

[21] Appl. No.: 212,782

[22] Filed: Dec. 4, 1980

[51] Int. Cl.$^4$ ............ C12N 9/00; C12N 9/14
[52] U.S. Cl. ................ 435/183; 435/195; 530/402
[58] Field of Search ........... 435/183, 184, 188, 200, 435/201, 213, 199, 195; 260/112-121; 530/350, 362, 402

[56] References Cited

U.S. PATENT DOCUMENTS

| | | | |
|---|---|---|---|
| 3,312,599 | 4/1967 | Kosland, et al. | 435/184 |
| 4,086,139 | 4/1978 | Hoerle | 435/184 |
| 4,258,030 | 3/1981 | Sasaki et al. | 435/184 |
| 4,609,625 | 9/1984 | Keyes et al. | 435/188 X |

OTHER PUBLICATIONS

Beaven et al., Modification of the Enzymic Activity of Trypsin by Intramolecular Cross-links, *Int. J. Peptide Protein Res.*, V5, 1973, pp. 215-218.
Yamauchi et al., Reversible Conversion of Lysine Monooxygenase to an Osidase by Modification of Sulfhydryl Groups, *J. Biol. Chem* V 248, 1973, pp. 3750-3752.
Perlmann, et al., *Methods in Enzymology*, vol. XIX, Proteolytic Enzymes, 1970, Academic Press, N.Y., pp. 57-58.
Dixon et al., *Enzymes VI*, Enzyme Specificity, 1964, Academic Press, N.Y., pp. 231-239, 2nd ed.
Mahler et al., *Biological Chemistry*, The Active Site of Enzymes, 1966, Harper & Row, N.Y., pp. 287-295.
Bruice et al., *Bioorganic Mechanisms*, vol. 1, 1966, W. A. Benjamin, N.Y., pp. 213-258.
Offord, *Semisynthetic Proteins*, Wiley and Sons, New York, 1980, p. 1-24.

*Primary Examiner*—David M. Naff
*Attorney, Agent, or Firm*—H. G. Bruss

[57] ABSTRACT

A naturally occurring protein is chemically modified to provide the protein with activity of a selected enzyme. The protein does not contain activity of the selected enzyme before modification. Modification is carried out by partially denaturing the protein, contacting the partially denatured protein with an enzyme inhibitor of the selected enzyme, crosslinking the protein in the presence of the inhibitor and recovering a modified protein having activity of the selected enzyme.

9 Claims, No Drawings

PROTEIN MODIFICATION TO PROVIDE ENZYME ACTIVITY

BACKGROUND OF THE INVENTION

1. Field of the Invention

Proteins are biologically synthesized macromolecules having various roles in living systems. Enzymes are a particular variety of biologically active proteins which catalyze specific reactions. Presently, enzyme technology is used in many areas in industry and research, such as, for example, medical research, food processing and preservation, the production of fermented beverages, the production of pharmaceuticals and the analytical determination of the concenration of various metabolites and food components by analytical enzyme techniques.

Enzymes are highly specific in their biological activity and generally catalyze a particular reaction at a very high rate compared to the corresponding reaction occurring at room temperature without biological catalysis. One enzyme may show catalytic activity with respect to a number of substrates upon which it can act. Accordingly, a given enzyme may catalyze the synthesis or degradation of more than one substrate. Some proteins which are not considered classicl enzymes, such as bovine serum albumin, show very limited catalytic activity with respect to one or more substrates.

Many enzymes are found in nature in very small quantities. Accordingly, their isolation, purification and use is limited to a small scale operations in view of the expense and time needed to isolate them in a useful form.

Some enzymes occur in nature in relatively large quantities and are relatively easy to isolate, purify and use. Unfortunately, due to the precise catalytic behavior of the enzymes, the enzymes available in large quantities can only catalyze certain select reactions.

Much effort has been directed in the recent past toward the snythesis of synthetic biological catalysts which exhibit enzymatic behavior similar to enzymatic behavior exhibited by native enzymes which are either scarce or expensive to isolate. Further, some attempts have been made to modify native enzymes to change their enzymatic specificity so that they may function to catalyze a reaction which they previously could not catalyze.

2. Description of the References

One technique known to achieve enzyme behavior to catalyze a specific desired reaction is the synthesis of so-called enzyme model molecules. For example, low molecular weight compounds may be covalently bonded to functional groups which exhibit the activity of the active site of an enzyme. Examples of such preparations are described in the publications: Breslow, R., *Advances In Chemistry Series,* R. F. Gould, Ed., American Chemical Society, Washington, D.C., 21–43 (1971) and Tang, C. C.; Davalian, D.; Haung, P, and Breslow, R. "*J. Amer. Chem. Soc.,* 100, 3918 (1978) and Breslow, R., Doherty, J. B., Guillot, G., and Lipsey, C.

Another technique involves the use of a synthetic polymer matrix which is modified along its backbone to provide functional groups which exhibit the function of the active site of a given enzyme. Examples of such techniques can be found in the following articles: Wulff, G. and Schulza, I., *Israel J. Chem.,* 17, 291 (1978) and Suh, J. and Klotz, I. M., *Bioorganic,* 6, 165 (1977).

Another technique involves the attachment of a new chemical moiety to a native enzyme near the active site of the enzyme to attempt to cause such enzyme to react with a different catalytic activity. One example of this is the conversion of papain, a proteolytic enzyme to an oxidase type enzyme by the covalent attachment of a flavin near the active site of the native papain enzyme, as illustrated in the articles: Levine, H. L. and Kaiser, E. T., *J. Amer. Chem. Soc.,* 100, 7670 (1978) and Otsuki, T.; Nakagawa, Y. and Kaiser, E. T., *J.C.S. Chem. Comm.,* 11, 457 (1978). Other examples of such enzymatic modification may be found in the article: Wilson, M. E. and Whitesides, G. M., *J. Amer. Chem. Soc.,* 100, 306 (1978).

Still another attempt to change enzyme specificity is the immobilization of a native enzyme into a gel matrix. For example, trypsin enzyme has been immobilized in polyacrylamide gel. The polyacrylamide gel allows amino acid esters to diffuse through the gel matrix to react with the enzyme but will not allow larger proteins to diffuse through. Thus, the enzyme specificity is changed by eliminating access of one of the substrate molecules to the enzyme. Examples of such specificity changes are described in the Kirk-Othmer *Encyclopedia of Chemical Technology,* 3 Ed., 9, 148 (1980) published by Wiley and Son, Inc.

Also, it has been known that a native lysine monooxygenase can be reacted to block the sulfhydryl groups on the enzyme. When the specific enzyme lysine monooxygenase is so treated, it shows new catalytic activity toward amino acids and catalyzes oxidative deamination instead of its natural oxygenative decarboxylation. However, the reporters cannot account for the modified behavior. See the article by Yamauchi, T.; Yamamoto, S. and Hayaishi, O., in *The Journal of Biological Chemistry,* 248, 10, 3750–3752 (1973). Also, it has been reported that by reacting a native enzyme, for example trypsin, with its natural inhibitor, and subsequently cross-linking the enzyme, its activity with respect to its natural substrates can be modified. See the article by Beaven, G. H. and Gratzer, W. B. in *Int. J. Peptide Res.,* 5, 215–18 (1973).

While these techniques are suitable for many applications, they generally produce modified natural enzymes or totally synthetic enzyme analogues which are not highly catalytically active. Accordingly, a need exists for a simple, efficient, and economical method for chemically modifying an inexpensive and commercially available native enzyme to produce a modified enzyme which shows an activity with respect to a desired chemical reaction which was not previously a commercially useful reaction catalyzed by the native enzyme and which new reaction can be predetermined in a systematic fashion. The methods disclosed in the above-described references simply subject an enzyme to a set of conditions and attempt to elucidate its behavior. They fail to present a systematic method to modify protein and enzyme behavior.

SUMMARY OF THE INVENTION

The present invention achieves a modified protein by subjecting a native protein, typically an enzymatically active protein, to partial denaturation by exposure to a denaturing agent, to partly unfold the conformational structure of the protein. Next, the partially denatured protein is contacted with an inhibitor of a model enzyme. Subsequently, the protein is cross-linked to define a new conformation or modified enzyme which is defined by the inhibitor. Then, the inhibitor and any excess cross-linking agent are removed from the newly formed modified enzyme to yield a functional analogue to the model enzyme. The modified enzyme thusly produced exhibits activity characteristic of the model enzyme.

DESCRIPTION OF THE PREFERRED EMBODIMENT

In attaining the objects and advantages of the present invention, it has now been discovered that a protein can be modified from its native conformation to a modified conformation by practicing the process of the present invention. The new conformational state defines the shape of a modified enzyme showing catalytic activity.

As used herein, the word "enzyme" is defined as a protein which has well known catalytic activity toward specific substrates. The term "protein" as used herein is defined as generally accepted in the art, to wit, a polypeptide formed of amino acids to yield a biological molecule.

The present invention comprises a process for modifying a protein from one conformation to a second conformation and thereby producing a new enzymatic activity for the selected protein or increasing a marginal enzymatic activity present in the native protein to a commercially useful level.

The process comprises subjecting a native protein, typically an enzyme, to conditions and/or reagents which will partially denature the structure of the protein, usually reversibly. Then, an inhibitor of the model enzyme is contacted with the native protein which is in the partially denatured state. While not being bound by any theory, it is believed that the partial denaturation of the protein allows the protein to bind an inhibitor of the enzyme to be modeled by the process to form an active site very similar to the active site of the model enzyme. The binding of the inhibitor is believed to preserve and define a new conformation which includes at least one site capable of performing the catalytic function of the model enzyme until the new conformation can be cross-linked. Accordingly, after the contacting of the inhibitor and the partially denatured protein is accomplished, a cross-linking step is conducted to chemically stabilize the new conformation of the protein. Thus, a new modified enzyme is prepared from a model protein.

As defined herein, "partial denaturation" means a change in the conformation of a protein so as to perturb the shape or conformation of the protein without causing an irreversible, gross denaturation of the protein. "Conformation" is defined, as generally accepted in the art, as that combination of secondary and tertiary structure of a protein which, in vivo, possesses biological activity. The partial denaturation of proteins is well known and discussed in detail in the following references: the book *Biochemistry*, by A. L. Lehninger, Worth Publishers, Inc., N.Y., 1970, pg. 58; the article by P. L. Privalov entitled "Stability of Proteins" in *Advances in Protein Chemistry*, Vol. 33, pg. 167-192; the article by C. Sanford entitled "Protein Denaturation, Part C" in *Advances in Protein Chemistry*, Vol. 24, pg. 2-97; the article by F. R. N. Gurd, et al entitled "Motions in Proteins" in *Advances in Protein Chemistry*, Vol. 33, pg. 74-166; the article by O. Jardetzky in *BBA*, Vol. 621, pg. 227-232; the article by R. Huber in *TIBS*, Dec. 1979, pg. 271, and the article by D. S. Markovich, et al in *Molekulyarnaya Biologiya*, Vol. 8, No. 6, pg. 857-863.

As used herein, the phrase "denaturing agent" refers to process conditions or reagents which cause the partial denaturation of a protein. For example, the partial denaturation of a protein can be accomplished by soaking the protein in an aqueous solution at elevated temperatures, for example, in the range of 25° C. to 60° C. For most proteins 25° C. to 60° C. will so perturb the structure of the protein as to result in partial denaturation of the protein. However, as is well known in the art, some proteins from thermophilic bacterial sources are stable to near the boiling point of water, and would require higher elevated temperatures than those generally disclosed above. Also, the partial denaturation of a protein can be accomplished by soaking the protein in an aqueous solution containing an inorganic salt, an inorganic or organic acid or a water-miscible solvent.

Suitable inorganic salts which serve to destabilize the protein structure include: NaF, $(NH_4)_2SO_4$, $(CH_3)_4NCl$, $(CH_3)_4NBr$, $KCH_3COO$, $NH_4Cl$, $RbCl$, $KCl$, $NaCl$, $CsCl$, $LiCl$, $KBr$, $NaBr$, $KNO_3$, $MgCl_2$, $NaNO_3$, $CaCl_2$, $KSCN$, $NaSCN$, $BaCl_2$, $NaI$, and $LiI$.

Suitable inorganic acids include: hydrochloric, nitric, sulfuric, phosphoric and similar proton donating strong inorganic acids.

Suitable organic acids include: acetic, formic, propionic and citric acid.

Suitable water-miscible solvents, which are believed to solubilize hydrophobic groups on the protein and thereby destabilize its structure, include: t-butanol, acetonitrile, dioxane, acetone, methanol, ethanol and dimethylsulfoxide.

As used herein, the term "inhibitor" means any compound with sufficient structural similarity to the natural substrate of a modified protein to serve as a template for the active site of a modified enzyme. Inhibitors are generally not degraded by the enzyme as are substrates. One example of the structural similarity of an enzyme inhibitor and the natural substrate of an enzyme is the case of glucose oxidase. Glucose is the natural substrate of glucose oxidase while D-glucal is the inhibitor for glucose oxidase. Glucose and D-glucal are very structurally similar.

As defined herein, the term "cross-linking" means the formation of covalent bonds either intermolecularly or intramolecularly between reactive sites on a protein. For intramolecular cross-linking, the process is usually accomplished by the use of multifunctional reagents such as glutaraldehyde. Other examples of suitable cross-linking reagents to effect a cross-linking of a protein are: 2-amino-4,6-dichloro-s-triazine; diazonium salts; N-hydroxy succinamide; p-benzoylazide and those reagents disclosed in the following references: Wold, F., *Methods Enzymol*, 11, HIRS, C. H. W. ed., Academic Press, 1967, 617; Fasold, H. et al, *Augen. Chem. Int. Ed. Engl.*, 10, 795, 197, and Keyes, M. H., *Kirk-Othmer: Encyclopedia of Chemical Technology*, 9, 3d ed., 1980, J. Wiley and Sons, Inc., 148–172.

Many naturally occurring enzymes would be susceptible to modeling by the present process to produce their modified analogues, for example, hydrolytic enzymes, redox enzymes and transferase enzymes. By way of example: The first group, hydrolytic enzymes include proteolytic enzymes which hydrolyze proteins, e.g., papain, ficin, pepsin, trypsin, chymotrypsin, bromelin, keratinase, carbohydrases which hydrolyze carbohydrates, e.g., cellulase, amylase, maltase, pectinase, chitanase; esterases which hydrolyze esters, e.g., lipase, cholinesterase, lecithinase, alkaline and acid phosphateases; nucleases which hydrolyze nucleic acid, e.g., ribuonclease, deoxyribonuclease; and amidases which hydrolyze amines, e.g., arginase, asparaginase, glutaminase, histidase, and urease. The second group are redox enzymes that catalyze oxidation or reduction reactions. These include glucose oxidase, xanthine oxidase, catalase, peroxidase, lipoxidase, and cytochrome reductase. In the third group are transferase enzymes that transfer groups from one molecule to another. Examples of these are glutamicpyruvic transaminase, glutamic-oxalacetic transaminase, transmethylase, phosphopyruvic transphosphorylase.

In the usual practice, one selects a model or first protein, typically an enzyme. Then one selects a second protein to be modeled after the first protein to produce a modified enzyme. By practicing the present invention, one can custom-tailor the second protein to a different, modified protein which is desired. This provides great advantage in a wide range of clinical and industrial situations in which the enzyme one wishes to use is in short supply, is very expensive or difficult to purify.

Thus, a native protein or enzyme which is available in large quantities and/or at low cost may be reformed or modified by the process of the present invention to convert the available protein or enzyme into a less available and/or more expensive modified enzyme which shows the catalytic activity of the desired native enzyme. There are many applications for such enzymatic conversion products such as, for example, many industrial and research applications particularly in fermentation, pharmaceuticals and medical research applications as well as food processing requirements.

In the usual practice of the invention, a native protein is purified and dissolved in a suitable buffer solution. Subsequently, the solution is admixed with a denaturing agent to partially denature the protein dissolved therein. Typically, the protein is partially denatured by changing the ionic strength of the solution by adding an inorganic salt, by modifying the pH of the solution with an inorganic or organic proton donating acid, or by modifying the solution by introducing a water-miscible organic solvent. The time of contacting of the denaturing agent and the protein can be from 15 minutes to a few days. Also, the temperature of the solution can be elevated as one process condition modification which will partially denature a protein as disclosed in the above references, for example, the article by Privalov. In some cases where the protein to be processed contains large numbers of disulphide bridges, for example, bovine serum albumin or urease, the partial denaturation may be effected by breaking disulphide linkages within the protein by subjecting the protein to mercapto-ethanol.

It is believed that the partial denaturation of the protein results in a loosening of the protein structure so that it may accept and bind the inhibitor which is subsequently admixed with the solution containing the partially denatured protein.

After the protein has been partially denatured, an inhibitor of the model enzyme is admixed and maintained in contact with the partially denatured enzyme for a time and at a temperature sufficient to establish a population of inhibitor-partially denatured enzyme complexes. For example, in the case of converting the native enzyme trypsin to a modified enzyme which models the activity of native enzyme chymotrypsin, the native enzyme trypsin is contacted with a chymotrypsin inhibitor, for example, indole or benzoic acid. The contacting may take place either in an aqueous solution or in an aqueous solution with added amounts of organic solvent sufficient to aid in the solubilization of the inhibitor.

After the contacting of the inhibitor with the partially denatured enzyme, the new shape of the modified enzyme is stabilized by extensive cross-linking of the protein structure. Typically, such cross-linking is done with glutaraldehyde cross-linking reagent since it is relatively inexpensive and readily available, but any of the above-described cross-linking reagents can be utilized successfully.

Subsequent to the cross-linking of the protein into the new structure to form the modified enzyme, the inhibitor and any excess cross-linking agent are removed from the newly formed modified enzyme by any suitable method. Liquid chromatography and exhaustive dialysis are suitable methods. Typically, the newly formed modified enzyme is purified by gel column chromatography and the most active protein fraction from the eluant is collected to provide the most active modified enzyme.

For convenience of disclosure, all of the patents and references noted herein are incorporated by reference.

The following Examples are illustrative of the process of the present invention.

EXAMPLE 1

Part A

Purification of the Enzyme

Purified trypsin, from bovine pancreas, twice crystallized, salt free and lyophilized, is tested according to the procedure of Kostka and Carpenter (Kostka, V. and Carpenter, F. H., *The Journal of Biological Chemistry*, 239, 6, 1799 (1964) and no native chymotrypsin contaminant is detected. The initial assay for trypsin substrate specificity is done by a potentiometric pH-Stat method according to the teaching of Walsh and Wilcox (Walsh, K. A. and Wilcox, P. E., *Methods in Enzymology*, edited by G. E. Perlmann and L. Lorand, Academic Press, 31–41 (1970)). The trypsin is prepared in 0.001M HCl at pH 3.0. The absorbance is determined at 280 nm and an absorbance of 14.3 for a 1% solution is used to establish the concentration in mg/ml.

Four initial potentiostatic pH-Stat assays were performed to determine the U/mg activity for each substrate of the native trypsin. The esterase substrates used were:
1. Acetyl tyrosine ethyl ester (ATEE)(0.01M)
2. Benzoyl arginine ethyl ester (BAEE)(0.01M)
3. Acetyl tryptophane ethyl ester (ATrEE)(0.01M)
4. Acetyl phenylalanine ethyl ester (APEE)(0.01M)

Part B

Denaturing the Enzyme

Sufficient purified trypsin of PART A is dissolved in 100 ml of 0.001M HCl at pH 3 at 25° C. to give an absorbance of 0.98 at 280 nm. The trypsin is allowed to stand for 30 minutes to partially denature.

Part C

Addition of Inhibitor

To 40 ml of the denatured enzyme solution of PART B is added 30 mg of purified dry indole powder and the mixture shaken slowly for 1 hour. After one hour the trypsin-chymotrypsin inhibitor complex is assayed to insure inhibition and thus the binding of the inhibitor to the enzyme.

Part D

Cross-Linking

To the solution of PART C is added 100 μl of 8% glutaraldehyde cross-linking agent. The resulting solution is shaken for 1 hour at 0°–5° C., at pH 3. After 1 hour the pH of the solution is raised to 5 by the addition of 0.01M NaOH.

Part E

Purification

Five ml of the solution of PART D is chromatographed on a Sephadex brand G-10 gel filtration column using 0.001M HCl, 0.001M in $CaCl_2$ as the eluant. Separation of the indole and the excess glutaraldehyde is accomplished in about one hour using a 12×1 inch column and an eluant flow rate of 60 ml/hr. The protein peak is detected at 254 nm and is collected and assayed as below described.

Part F

Results

The following increase in activity with respect to substrate for chymotrypsin is recorded from samples from PART E of the chymotrypsin like modified protein prepared according to the invention.

|  | Substrate ATEE (U/mg) | BAEE (U/mg) |
|---|---|---|
| Initial Activity | 5.21 | 55.3 |
| Final Activity Assay Procedure One | 8.37 | 30.21 |
| Percent Change | +160 | −46 |

The results show that the chymotrypsin like modified protein exhibits increased activity with respect to chymotrypsin subsrate (ATEE) and reduced activity with respect to trypsin substrate (BAEE).

This Example also illustrates a substantial increase in activity with respect to a substrate when using the process of the present invention. This Example further illustrates the increase in activity of one species of peptidyl-peptide hydrolase, namely trypsin, with respect to the native ester hydrolysis catalytic activity, toward the substrate of another peptidyl-peptide hydrolase, namely chymotrypsin, with respect to the native esterase type activity of chymotrypsin when processed according to the invention to produce a chymotrypsin like modified protein.

EXAMPLE 2

Part A

Purification of the Enzyme

Ribonuclease enzyme is purchased in purified form as salt free, protease free bovine pancreas ribonuclese, Type II-A from Sigma Chemical Co.

Part B

Denaturing the Enzyme

Sixty mg of purified ribonuclease from PART A is dissolved in 100 ml of deionized distilled water and exhibits an absorbance of 0.39 at 280 nm. To the solution is added 300 μl of 0.2M mercaptoethanol denaturing agent. The pH of the solution is raised to 7 and maintained thereat for two hours with slow stirring at 25° C. by the dropwise addition of 0.01M NaOH.

Part C

Addition of Inhibitor

To the 100 ml of solution from PART B is added 20 mg of dry powdered indole inhibitor. The solution is stirred at 25° C. and maintained at pH 7 by the dropwise addition of 0.01M NaOH for 1–1.5 hours until all the indole is in solution.

Part D

Cross-Linking

The solution of PART C at 25° C. is raised to pH 9.45 with the dropwise addition of 0.1M NaOH and stirred slowly for 3 hours. Then the solution is cooled to 0°–5° C. in a cold water bath. When the solution reaches 5° C., in about 30 minutes usually, 400 μl of an 8% glutaraldehyde cross-linking agent is added and the solution slowly shaken for 17 hours.

Part E

Purification

Five ml of the solution of PART D is chromatographed on a Sephadex brand G-15 column using 0.001M HCl eluant. Separation of the indole and the excess glutaraldehyde is accomplished using a 12×1 inch column. The protein fraction is collected by monitoring at 206 nm.

Part F

Results

The following increase in activity with respect to substrate for esterase is recorded from samples from PART E of the esterase like modified protein prepared according to the invention.

|  | Substrate BAEE (U/mg) |
|---|---|
| Initial Activity | 0.00 |
| Final Activity |  |
| Assay Procedure One | 0.3 |
| Assay Procedure Two | 0.4 |
| Percent Change | N/A |

The results show that the esterase like modified protein shows enzymatic activity toward the esterase substrate where no activity was detected in the native ribonuclease. This illustrates the conversion of one genus of enzyme, a nuclease, to another genus of enzyme, an esterase.

EXAMPLE 3

Part A

Purification of the Enzyme

Purified trypsin, from bovine pancreas, twice crystallized, salt free and lyophilized, is tested according to the procedure of Kostka and Carpenter (Kostka, V. and Carpenter, F. H., *The Journal of Biological Chemistry*, 239, 6, 1799 (1964)) and no native chymotrypsin contaminant is detected. The initial assay for trypsin substrate specificity is done by a potentiometric pH-Stat method according to the teaching of Walsh and Wilcox (Walsh, K. A. and Wilcox, P. E., *Methods in Enzymology*, edited by G. E. Perlmann and L. Lorand, Academic Press, 31–41 (1970). The trypsin is prepared in 0.001M HCl at pH 3.0. The absorbance is determined at 280 nm and an absorbance of 14.3 for a 1% solution is used to establish the concentration in mg/ml.

Four initial potentiostatic pH-Stat assays were performed to determine the U/mg activity for each substrate of the native trypsin. The esterase substrates used were:

1. Acetyl tyrosine ethyl ester (ATEE)(0.01M)
2. Benzoyl arginine ethyl ester (BAEE)(0.01M)
3. Acetyl tryptophane ethyl ester (ATrEE)(0.01M)
4. Acetyl phenylalanine ethyl ester (APEE)(0.01M)

Part B

Denaturing the Enzyme

Sufficient purified trypsin of PART A is dissolved in 100 ml of 0.001M HCl at pH 3 at 25° c. to give an absorbance of 1.4 at 280 nm. The trypsin is allowed to stand for 30 minutes to partially denature.

Part C

Addition of Inhibitor

To 40 ml of the denatured enzyme solution of PART B is added 2 ml of 1% indole solution (in 0.001M HCl) and the solution shaken slowly for 2 hours. After two hours the trypsin-chymotrypsin inhibitor complex is assayed to insure inhibition and thus the binding of the inhibitor to the enzyme.

Part D

Cross-Linking

To the solution of PART C is added 300 μl of 8% glutaraldehyde cross-linking agent. The resulting solution is shaken for 17 hours at 0°–5° C., at pH 3. After 17 hours the pH of the solution is raised to 5 by the addition of 0.01M NaOH.

Part E

Purification

Five ml of the solution of PART D is chromatographed on a Sephadex brand G-10 gel filtration column using 0.001M HCl, 0.001M in CaCl₂ as the eluant. Separation of the indole and the excess glutaraldehyde is accomplished in about one hour using a 12×1 inch column and an eluant flow rate of 60 ml/hr. The protein peak is detected at 254 nm and is collected and assayed as below described.

Part F

Results

The following increase in activity with respect to substrate for chymotrypsin like modified protein is recorded from samples from Part E of the semisynthetic chymotrypsin prepared according to the invention.

|  | Substrate ATEE (U/mg) | BAEE (U/mg) |
|---|---|---|
| Initial Activity | 3.2 | 52.0 |
| Final Activity Assay Procedure One | 12.85 | 45.75 |
| Percent Change | +401 | −14 |

The results show that the chymotrypsin like modified protein exhibits increased activity with respect to chymotrypsin substrate (ATEE) and reduced activity with respect to trypsin substrate (BAEE).

This Example also illustrates a substantial increase in activity with respect to a substrate when using the process of the present invention. This Example further illustrates the increase in activity of one species of peptidyl-peptide hydrolase, namely trypsin, with respect to the native ester hydrolysis catalytic activity toward the substrate of another peptidyl-peptide hydrolase, namely chymotrypsin, with respect to the native esterase activity of chymotrypsin when processed according to the invention.

EXAMPLE 4

Part A

Purification of the Protein

Bovine serum albumin (BSA) protein is purchased in purified form as crystalline, lyophilized protein with 1–3% globulins as purchased from Sigma Chemical Co., lot A4378.

Part B

Denaturing the Enzyme

One hundred mg of purified BSA from PART A is dissolved in 100 ml of deionized distilled water and exhibits an absorbance of 0.58 at 280 nm. The pH of the solution is maintained at pH 3 for two hours with slow stirring at 25° C. by the dropwise addition of 0.01M HCl.

Part C

Addition of Inhibitor

To the 100 ml of solution from PART B is added 40 mg of dry powdered indole inhibitor. The solution is stirred at 25° C. and maintained at pH 3 by the dropwise addition of 0.01M HCl for 1–1.5 hours until all the indole is in solution.

Part D

Cross-Linking

The solution of PART C at 25° C. is raised to pH 7 with the dropwise addition of 0.1M NaOH and stirred slowly for 3 hours. Then the solution is cooled to 0°–5° C. in a cold water bath. When the solution reaches 5° C., in about 30 minutes usually, 400 μl of an 8% glutaralehyde cross-linking agent is added and the solution slowly shaken for 17 hours.

Part E

Purification

Five ml of the solution of PART D is chromatographed on a Sephadex brand G-15 gel column using 0.001M HCl eluant. Separation of the indole and the excess glutaraldehyde is accomplished using a 12×1 inch column. The protein fraction is collected by monitoring at 206 nm.

Part F

Results

The following increase in activity with respect to substrate for esterase is recorded from samples from PART E of the esterase like modified protein prepared according to the invention.

|  | Substrate BAEE (U/mg) |
|---|---|
| Initial Activity | 0.00 |
| Final Activity |  |
| Assay Procedure One | 0.06 |
| Assay Procedure Two | 0.022 |
| Percent Change | N/A |

The results show that the esterase like modified protein shows enzymatic activity toward the esterase substrate where no activity was detected in the native BSA. This illustrates the conversion of one genus of nonenzymatic protein, an albumin, to another genus of protein, an enzymatically active esterase.

EXAMPLE 5

Part A

Purification of the Enzyme

Purified trypsin, from bovine pancreas, twice cyrstallized, salt free and lyophilized, is tested according to the procedure of Kostka and Carpenter (Kostka, V. and Carpenter, F. H., *The Journal of Biological Chemistry*, 239, 6, 1799 (1964)) and no native chymotrypsin containment is detected. The initial assay for trypsin substrate specificity is done by a potentiometric pH-Stat method according to the teaching of Walsh and Wilcox (Walsh, K. A. and Wilcox, P. E., *Methods in Enzymology*, edited by G. E. Perlman and L. Lorand, Academic Press, 31–41 (1970)). The trypsin is prepared in 0.001M HCl at pH 3.0. The absorbance is determined at 280 nm and an absorbance of 14.3 for a 1% solution is used to establish the concentration in mg/ml.

Four initial potentiostatic pH-Stat assays were performed to determine the U/mg activity for each substrate of the native trypsin. The esterase substrates used were:
1. Acetyl tyrosine ethyl ester (ATEE) (0.01M)
2. Benzoyl arginine ethyl ester (BAEE) (0.01M)
3. Acetyl tryptophane ethyl ester (ATrEE) (0.01M)
4. Acetyl phenylalanine ethyl ester (APEE) (0.01M)

Part B

Denaturing the Enzyme

Sufficient purified trypsin of PART A is dissolved in 100 ml of 0.001M HCl at pH 3 at 25° C. to give an absorbance of 0.98 at 280 nm. The trypsin is allowed to stand for 30 minutes to partially denature.

Part C

Addition of Inhibitor

To 40 ml of the denatured enzyme solution of PART B is added 2 ml of 1% indole (in 0.001M HCl) and the solution shaken slowly for 1 hour.

Part D

Cross-Linking

To the solution of PART C is added 100 μl of 8% glutaraldehyde cross-linking agent. The resulting solution is shaken for 20 hours at 0°–5° C., at pH 3. After 20 hours the pH of the solution is raised to 5 by the addition of 0.01M NaOH.

Part E

Purification

Five ml of the solution of PART D is chromatographed on a Sephadex brand G-10 gel filtration column using 0.001M HCl, 0.001M in $CaCl_2$ as the eluant. Separation of the indole and the excess glutaraldehyde is accomplished in about one hour using a 12×1 inch column and an eluant flow rate of 60 ml/hr. The protein peak is detected at 254 nm and is collected and assayed as below described.

Part F

Results

The following increase in activity with respect to substrate for chymotrypsin is recorded from samples from PART E of the chymotrypsin like modified protein prepared according to the invention.

| | Substrate | |
|---|---|---|
| | ATEE (U/mg) | BAEE (U/mg) |
| Initial Activity | 3.2 | 52.0 |
| Final Activity | 8.45 | 48.0 |
| Assay Procedure One | | |
| Percent Change | +264 | −8 |

The results show that the semisynthetic chymotrypsin exhibits increased activity with respect to chymotrypsin substrate (ATEE) and reduced activity with respect to trypsin substrate (BAEE).

This Example also illustrates a substantial increase in activity with respect to a substrate when using the process of the present invention. This Example further illustrates the increase in activity of one species of peptidyl-peptide hydrolase, namely trypsin, with respect to the native ester hydrolysis catalytic activty, toward the substrate of another peptidyl-peptide hydrolase, namely chymotrypsin, with respect to the native esterase type activity of chymotrypsin, when processed according to the invention.

EXAMPLE 6

Part A

Purification of the Enzyme

Purified trypsin, from bovine pancreas, twice crystallized, salt free and lyophilized, is tested according to the procedure of Kostka and Carpenter (Kostka, V. and Carpenter, F. H., *The Journal of Biological Chemistry*, 239, 6, 1799 (1964)) and no native chymostrypsin contaminant is detected. The initial assay for trypsin substrate specificity is done by a potentiometric pH-Stat method according to the teaching of Walsh and Wilcox (Walsh, K. A. and Wilcox, P. E., *Methods in Enzymology*, edited by G. E. Perlmann and L. Lorand, Academic Press, 31–41 (1970)). The trypsin is prepared in 0.001M HCl at pH 3.0. The absorbance is determined at 280 nm and an absorbance of 14.3 for a 1% solution is used to establish the concentration in mg/ml.

Four initial potentiostatic pH-Stat assays were performed to determine the U/mg activity for each substrate of the native trypsin. The esterase substrates used were:
1. Acetyl tryosine ethyl ester (ATEE) (0.01M)
2. Benzoyl arginine ethyl ester (BAEE) (0.01M)
3. Acetyl tryptophane ethyl ester (ATrEE) (0.01M)
4. Acetyl phenylalanine ethyl ester (APEE) (0.01M)

Part B

Denaturing the Enzyme

Sufficient purified trypsin of PART A is dissolved in 100 ml of 0.001M HCl at pH 3 at 25° C. to give an absorbance of 1.35 at 280 nm. The trypsin is allowed to stand for 30 minutes to partially denature.

Part C

Addition of Inhibitor

To 10 ml of the denatured enzyme solution of PART B is added 5 ml of 1% benzoic acid in water and the solution shaken slowly for 1 hour. After one hour the trypsin-chymotrypsin inhibitor complex is assayed to insure inhibition and thus the binding of the inhibitor to the enzyme.

Part D

Cross-Linking

To the solution of PART C is added 100 µl of 8% glutaraldehyde cross-linking agent. The resulting solution is shaken for 17 hours at 0°–5° C., at pH 3. After 17 hours the pH of the solution is raised to 5 by the addition of 0.01M NaOH.

Part E

Purification

Five ml of the solution of PART D is chromatographed on a Sephadex brand G-10 gel filtration column using 0.001M HCl, 0.001M in $CaCl_2$ as the eluant. Separation of the benzoic acid and the excess glutaraldehyde is accomplished in about one hour using a 12×1 inch column and an eluant flow rate of 60 ml/hr. The protein peak is detected at 254 nm and is collected and assayed as below described.

Part F

Results

The following increase in activity with respect to substrate for chymotrypsin is recorded from samples from PART E of the chymostrypsin like modified protein prepared according to the invention.

|  | Substrate ATrEE (U/mg) |
| --- | --- |
| Initial Activity | 1.66 |
| Final Activity | 6.35 |
| Assay Procedure One |  |
| Percent Change | +382 |

The results show that the chymotrypsin like modified protein exhibits increased activity with respect to chymotrypsin substrate (ATEE) and reduced activity with respect to trypsin substrate (BAEE).

This Example also illustrates a substantial increase in activity with respect to a substrate when using the process of the present invention. This Example further illustrates the increase in activity of one species of peptidyl-peptide hydrolase, namely trypsin, with respect to the native ester hydrolysis catalytic activity, toward the substrate of another peptidyl-peptide hydrolase, namely chymotrypsin, with respect to the native esterase type activity of chymotrypsin, when processed according to the invention.

EXAMPLE 7

Part A

Purification of the Enzyme

Ribonuclease enzyme is purchased in purified form as salt free, protease free bovine pancreas ribonuclease, Type II-A from Sigma Chemical Co.

Part B

Denaturing the Enzyme

Sixty mg of purified ribonuclease from PART A is dissolved in 100 ml of deionized distilled water and exhibits an absorbance of 0.411 at 280 nm. The pH of the solution is lowered to 3 and maintained thereat for two hours with slow stirrring at 25° C. by the dropwise addition of 0.01M HCl.

Part C

Addition of Inhibitor

To the 100 ml of solution from PART B is added 40 mg of dry powdered indole inhibitor. The solution is stirred at 25° C. and maintained at pH 3 by the dropwise addition of 0.01M HCl for 1–1.5 hours until all the indole is in solution.

Part D

Cross-Linking

The solution of PART C at 25° C. is raised to pH 7 with the dropwise addition of 0.1M NaOH and stirred slowly for 3 hours. Then the solution is cooled to 0°–5° C. in a cold water bath. When the solution reaches 5° C., in about 30 minutes usually, 400 µl of an 8% glutaraldehyde cross-linking agent is added and the solution slowly shaken for 30 hours.

Part E

Purification

The solution from PART D is dialyzed against 0.01M Tris buffer at pH 7 using Spectrapore brand tubing having a molecular weight cutoff of about 3500 for 20 hours at 0°–5 ° C.

Part F

Results

The following increase in activity with respect to substrate for esterase is recorded from samples from PART E of the esterase like modified protein prepared according to the invention. The buffer described in assay procedure two is adjusted to the proper pH with 0.01M HCl.

|  | Substrate BAEE (U/mg) |
| --- | --- |
| Initial Activity | 0.00 |
| Final Activity |  |
| Assay Procedure Two | pH 9 .089 |
|  | pH 8 .15 |
|  | pH 7 .29 |
|  | pH 6 .79 |
|  | pH 5 .41 |
| Percent Change | N/A |

The results show that the esterase like modified protein shows enzymatic activity toward the esterase substrate where no activity was detected in the native ribonuclease. This illustrates the conversion of one genus of enzyme, a nuclease, to another genus of enzyme, an esterase.

EXAMPLE 8

Part A

Purification of the Enzyme

Purified trypsin, from bovine pancreas, twice crystallized, salt free and lyophilized, is tested according to the procedure of Kostka and Carpenter (Kostka, V. and Carpenter, F. H., *The Journal of Biological Chemistry*, 239, 6, 1979 (1964)) and no native chymotrypsin contaminant is detected. The initial assay for trypsin substrate specificity is done by a potentiometric pH-Stat method according to the teaching of Walsh and Wilcox (Walsh, K. A. and Wilcox, P. E., *Methods in Enzymology*, edited by G. E. Perlmann and L. Lorand, Academic Press, 31–41 (1970)). The trypsin is prepared in 0.001M HCl at pH 3.0. The absorbance is determined at 280 nm and an absorbance of 14.3 for a 1% solution is used to establish the concentration in mg/ml.

Four initial potentiostatic pH-Stat assays were performed to determine the U/mg activity for each substrate of the native trypsin. The esterase substrates used were:
1. Acetyl tryosine ethyl ester (ATEE) (0.01M)
2. Benzoyl arginine ethyl ester (BAEE) (0.01M)
3. Acetyl tryptophane ethyl ester (ATrEE) (0.01M)
4. Acetyl phenylalanine ethyl ester (APEE) (0.01M)

Part B

Denaturing the Enzyme

Sufficient trypsin of PART A is dissolved i 100 ml of 0.001M HCl at pH 3 at 25° C. to give an absorbance of 1.56 at 280 nm. The trypsin is allowed to stand for 30 minutes to partially denature.

Part C

Addition of Inhibitor

To 40 ml of the denatured enzyme solution of PART B is added 2 ml of neat phenyl acetate and the solution is readjusted to pH 3 with dilute HCl. Then the solution is heated to 40° C. to dissolve all the phenyl acetate inhibitor into the solution and stirred for 2 hours.

Part D

Cross-Linking

To the solution of PART C is added 600 μl of 8% glutaraldehyde cross-linking agent. The resulting solution is shaken for 20 hours at 0°–5° C., at pH 3.

Part E

Purification

Five ml of the solution of PART D is chromatographed on a Sephadex brand G-10 gel filtration column using 0.001M HCl, 0.001M in $CaCl_2$ as the eluant. Separation of the phenyl acetate and the excess glutaraldehyde is accomplished in about one hour using a 12×1 inch column and an eluant flow rate of 60 ml/hr. The protein peak is detected at 254 nm and is collected and assayed as below described.

Part F

Results

The following increase in activity with respect to substrate for chymotrypsin is recorded from samples from PART E of the semisynthetic chymotrypsin prepared according to the invention.

|  | Substrate ATEE (U/mg) | BAEE (U/mg) |
|---|---|---|
| Initial Activity | 3.2 | 54 |
| Final Activity Assay Procedure One | 6.23 | 32.6 |
| Percent Change | +195 | −22 |

The results show that the chymotrypsin like modified protein exhibits increased activity with respect to chymotrypsin substrate (ATEE) and reduced activity with respect to trypsin substrate (BAEE).

This Example also illustrates a substantial increase in activity with respect to a substrate when using the process of the present invention. This Example further illustrates the increase in activity of one species of peptidyl-peptide hydrolase, namely trypsin, with respect to the native ester hydrolysis catalytic activity toward the substrate of another peptidyl-peptide hydrolase, namely chymotrypsin, with respect to the native esterase type activity of chymotrypsin, when processed according to the invention.

EXAMPLE 9

Part A

Purification of the Enzyme

Bacterial alpha-amylase is purchased as purified enzyme, four times crystallized material, Type II-A from Sigma Chemical Co., isolated from *Bacillus subtilis*.

One gram of purified bacterial alpha-amylase is dissolved in 100 ml of deionized distilled water and dialyzed against 1 mM phosphate buffer at pH 7 for 24 hours at 0°–5° C. Then the preparation is frozen until use.

Part B

Denaturing the Enzyme

Ten ml of the frozen 1% alpha-amylase from PART A is brought to room temperature and filtered through a 0.20 μm pore size filter. The concentration is determined to be 0.67 percent after storage. Then 6.5 ml of the alpha-amylase solution is titrated with 0.01M NaOH to a pH of 10.7 and stirred slowly for ten minutes.

Part C

Addition of Inhibitor

The solution of PART B is admixed with 0.017 grams of cellobiose inhibitor and stirred for 45 minutes at 25° C.

Part D

Cross-Linking

The solution from PART C at 25° C. is admixed with 10 μl of glutaraldehyde cross-linking agent and stirred for 15 minutes. At the addition of the glutaraldehyde the pH dropped to 9.9 and the solution yellowed from clear. The pH is adjusted to 9 with 0.01M HCl in dropwise fashion and stirred for an additional 15 minutes. The pH is then adjusted slowly to 7 with 0.01M HCl and stirred for one additional hour.

Part E

Purification

Five ml of the solution from PART D is chromatographed on a Sephadex brand G-10 gel filtration column 1.25×47 cm and using 0.01M, pH 7 Tris buffer at flow rate 1 ml/min. The protein peak is detected at 206 nm and collected.

Part F

Results

The following increase in activity with respect to the substrate for glycoside hydrolase is recorded from samples from PART E of the glycoside hydrolase like modified protein prepared according to the invention. The substrates of glycoside hydrolase used are:

p-nitrophenyl-β-D-galacto pyranoside (pNβGA) and
p-nitrophenyl-α-D-glucoside (pNαGL)

|  | Substrate | |
|---|---|---|
|  | pNβGA (U/ml) | pNαGL (U/ml) |
| Initial Activity | 0.00 | 0.00 |
| Final Activity |  |  |
| Assay Procedure Three | $1.8 \times 10^{-3}$ | $1.5 \times 10^{-3}$ |
| Assay Procedure Four | $3 \times 10^{-3}$ |  |

The results show that the glycoside hydrolase like modified protein shows enzymatic activity toward the glycoside hydrolase substrate where no activity was detected in the native bacterial alpha-amylase, itself a species of glycoside hydrolase. This illustrates the conversion of one glycoside hydrolase to another glycoside hydrolase.

EXAMPLE 10

Part A

Purification of the Enzyme

Bacterial alpha-amylase is purchased as purified enzyme, four times crystallized material, Type II-A from Sigma Chemical Co., isolated from *Bacillus subtilis.*

Fifteen hundredths of a gram of purified bacterial alpha-amylase is dissolved in 15 ml of deionized distilled water and dialyzed against 1 mM phosphate buffer at pH 7 for 24 hours at 0°–5° C.

Part B

Denaturing the Enzyme

Ten ml of the 1% alpha-amylase solution from PART A is brought to room temperature and centrifuged at 20,000 gravity forces for 20 minutes. The concentration is determined to be 0.65 percent. Then 10 ml of the alpha-amylase solution is titrated with 0.01M NaOH to a pH of 10.6 and stirred slowly for 10 minutes.

Part C

Addition of Inhibitor

The solution of PART B is admixed with 0.051 grams of cellobiose inhibitor and stirred for 45 minutes at 25° C.

Part D

Cross-Linking

The solution from PART C at 25° C. is admixed with 86 μl of glutaraldehyde cross-linking agent. Immediately following 0.1M solution of $NaCO_3$—$NaHCO_3$, pH 10.0 is added until pH is maintained at 10 for 15 minutes. Approximately 0.7 ml of carbonate solution was added.

Part E

Purification

One ml of the solution from PART D is chromatographed on a Sephadex brand G-10 gel filtration column 1.25×47 cm and using 0.01M, pH 7 Tris buffer at flow rate 0.34 ml/min. The protein peak is detected at 254 nm and collected.

Part F

Results

The following increase in activity with respect to the substrate for glycoside hydrolase is recorded from samples from PART E of the glycoside hydrolase like modified protein prepared according to the invention. The substrates for glycoside hydrolase used are:

p-nitrophenyl-β-D-glucoside (pNβGL) and
p-nitrophenyl-α-D-glucoside (pNαGL)

|  | Substrate pNβGL (U/mg) | pNαGL (U/mg) |
|---|---|---|
| Initial Activity | 0.00 | 0.00 |
| Final Activity | $3.1 \times 10^{-4}$ | $1.4 \times 10^{-4}$ |
| Assay Procedure Five | | |

The results show that the glycoside hydrolase like modified protein shows enzymatic activity toward the glycoside hydrolase substrate where no activity was detected in the native bacterial alpha-amylase, itself a species of glycoside hydrolase. This illustrates the conversion of one glycoside hydrolase to another glycoside hydrolase.

EXAMPLE 11

Part A

Purification of the Enzyme

Bacterial alpha-amylase is purchased as purified enzyme, four times crystallized material, Type II-A from Sigma Chemical Co., isolated from *Bacillus subtilis.*

Fifteen hundredths of a gram of purified bacterial alpha-amylase is dissolved in 15 ml of deionized distilled water and dialyzed against 1 mM phosphate buffer at pH 7 for 24 hours at 0°–5° C.

Part B

Denaturing the Enzyme

Ten ml of the 1% alpha-amylase from PART A is brought to room temperature and centrifuged at 20,000 gravity forces for 20 minutes. The concentration is determined to be 0.57 percent. Then 10 ml of the alpha-amylase solution is titrated with 0.01N NaOH to a pH of 10.6 and stirred slowly for 10 minutes.

Part C

Addition of Inhibitor

The solution of PART B is admixed with 0.051 grams of cellobiose inhibitor and stirred for 45 minutes at 25° C.

Part D

Cross-Linking

The solution from PART C at 25° C. is admixed with 72 μl of glutaraldehyde cross-linking agent. Immediately following 0.1M $NaCO_3$—$NaHCO_3$ solution, pH 10.0 is added until the pH is maintained at 10.0 for 15 minutes. Four tenths ml of carbonate solution was used.

Part E

Purification

One ml of the solution from PART D is chromatographed on a Sephadex brand G-10 gel filtration column 1.25×47 cm using 0.01M, pH 7 Tris buffer at flow rate 0.34 ml/min. The protein peak is detected at 254 nm and collected.

Part F

Results

The following increase in activity with respect to the substrate for glycoside hydrolase is recorded from samples from PART E of the glycoside hydrolase like modified protein prepared according to the invention. The substrate for glycoside hydrolase used is:

p-nitrophenyl-β-D-glucoside (pNβGL)

|  | Substrate pNβGL (U/mg) |
|---|---|
| Initial Activity | 0.00 |
| Final Activity | $2.8 \times 10^{-4}$ |
| Assay Procedure Five | |

The results show that the glycoside hydrolase like modified protein shows enzymatic activity toward the glycoside hydrolase substrate where no activity was detected in the native bacterial-alpha-amylase, itself a species of glycoside hydrolase. This illustrates the conversion of one glycoside hydrolase to another glycoside hydrolase.

ASSAY PROCEDURES

The samples in EXAMPLES 1–8 can be assayed by one of two methods. Assay method one measures proton release from reacting substrate. Assay method two measures spectral changes from electronic structure changes induced by hydrolysis of substrate. In all cases of EXAMPLES 1–8 above, either method produced a positive activity change measurement with respect to the activity desired to be modeled, confirming by two unrelated measurement techniques the fact of activity creation where none previously existed.

EXAMPLE OF ASSAY PROCEDURE ONE

Reagents:
  0.1M KCl, 0.05M $CaCl_2$, 0.01M Tris buffer at pH 7.75.
Substrate:
  Dissolve 343 mg of alpha-N-benzoyl-L-arginine ethyl ester HCl (BAEE) in 100 ml buffer.
Procedure:
  Using a Sargent-Welch pH-Stat model pHR, fill the titration buret with 0.1M NaOH. Place 5 ml of substrate solution in the pH-Stat beaker on fast stir. Adjust titrator to raise the pH to 7.8. Establish a firm baseline. Add 2 ml of enzyme solution. The Recorder traces the volume of any base consumed per unit time as a direct measure of micromoles of substrate consumed per minute.

EXAMPLE OF ASSAY PROCEDURE TWO

Reagents:
  0.1M KCl, 0.05M $CaCl_2$, 0.5M Tris buffer at pH 8.0.
Substrate:
  Dissolve 34.3 mg of alpha-N-benzoyl-L-arginine ethyl ester HCl (BAEE) in 100 ml buffer.
Procedure:
  Using a Beckman ACTA Spectrophotometer set the wavelength adjuster at 255 nm at a slit width of 1.25 nm. Adjust the zero buffer in the reference and sample. Empty the sample chamber and wash the cuvette with acetone, then with water. Add 2.5 ml BAEE substrate solution and a one minute baseline. Add 0.5 ml of solution enzyme and record the rate of increase in absorbance as BAEE is hydrolyzed to alpha-N-benzoyl-L-arginine. Plot absorbancy versus time (delta A/min) for at least 5 minutes. With delta absorptivity substrate-product at 808 $M^{-1} cm^{-1}$, one unit is equal to the hydrolysis of one micromole of BAEE per minute at 25° C. and pH 8.0.

See Schwert, G. W. and Takenake, T., Biochemica et Biophsica ACTA, 16, 570, 1955.

EXAMPLE OF ASSAY PROCEDURE THREE

The samples assayed in Example 9 can be assayed by the below described procedure.
Reagents:
  Sodium citrate buffer 0.05M at pH 4.6.
  Sodium carbonate at 0.2M.
Substrate:
  $p$-nitrophenyl-$\alpha$-D-glucoside 25 mM solution in 0.05M sodium citrate buffer at pH 4.6.
  $p$-nitrophenyl-$\alpha$-D-galacto pyranoside 25 mM solution in 0.05M sodium citrate buffer at pH 4.6.
Procedure:
  A 100 $\mu$l sample of a 25 mM solution of either substrate in 0.05M sodium citrate buffer at pH 4.6 is incubated at 30° C. with 350 $\mu$l of the same buffer for 5 minutes. Five such solutions were prepared. After the addition of 50 $\mu$l of enzyme to three of the solutions and 50 $\mu$l of citrate buffer to the two remaining control solutions, the solution is incubated at 30° C. At 15 minutes, one solution containing enzyme and one control are selected. The reaction is stopped by adding 700 $\mu$l of 0.2M sodium carbonate. The absorbance is measured at 420 nm. At 30 minutes, another enzyme solution is analyzed and at 60 minutes the last enzyme solution and the remaining control are analyzed.

See *Methods in Enzymology*, Vol. 28, pg. 720–21.

The activities are calculated using an absorptivity of $1.82 \times 10^{+4} M^{-1} cm^{-1}$.

See *J. Biol. Chem.*, 233, 1113 (1958).

The absorbance of 25.2 at 280 nm for a 1% solution of $\alpha$-amylase is used to calculate the amount of enzyme present.

EXAMPLE OF ASSAY PROCEDURE FOUR

High Pressure Liquid Chromatography Assay

The samples assayed in EXAMPLE 9 can be assayed by the below described procedure.
Reagents:
  Galactose, 0.1% solution.
  Galactose, 1.0% solution.
  $p$-nitrophenyl-$\beta$-D-galacto pyranoside ($pN\beta GL$), 12 mM solution.
  $p$-nitrophenol, 0.5% solution.
  Glucosidase, 0.5% solution.
  Micro-Pak brand (Varian Associates) column 30×4 cm.
  Absorbance Detector set at 206 mM.
  Water eluant at 25° C.
  Flow—2.5 ml/minute at 2,000 psi.
Procedure:
  A mixture of semisynthetic glycoside hydrolase and $pN\beta GL$ was incubated and subsequently applied to the column. At 18 hours a peak at the position established for galactose was recorded. From standard galactose solutions, the peak height and concentration were determined. The activity of the semisynthetic enzyme was calculated to be $3 \times 10^{-3}$ U/ml.

EXAMPLE OF ASSAY PROCEDURE FIVE

The samples assayed in EXAMPLES 10 and 11 can be assayed by the below described procedure.
Reagents:
  Sodium citrate buffer 0.05M at pH 5.0.
  Sodium carbonate at 0.2M.
Substrate:
  $p$-nitrophenyl-$\beta$-D-gluco pyranoside.
  25 mM solution dissolved in deionized distilled water.
  $p$-nitrophenyl-$\beta$-D-gluco pyranoside.
  25 mM solution dissolved in deionized distilled water.
Procedure:
  A 700 $\mu$l aliquot of sodium citrate buffer, pH 5, is added to five tubes, two of which are controls. One hundred $\mu$l of the semisynthetic enzyme is added to three such tubes, while 100 $\mu$l of sodium citrate pH 5 is added to the two controls. These tubes are incubated for 10 minutes in a 30° C. shaker. After the 10 minute period, 200 μl of the appropriate substrate is added to all five tubes and allowed to incubate in a 30° C. shaker. After 15 minutes of incubation, one control tube and one tube containing enzyme are taken out. The solution in the control tube is immediately mixed with 1.4 ml of 0.2M sodium carbonate. The tube containing enzyme is centrifuged for 2 minutes. After the 2 minute period, the liquid in the tube is poured into a marked tube and the precipitate is discarded. Then 500 μl of the solution is pipetted into another marked tube and 700 μl of 0.2M sodium carbonate buffer is added to stop the reaction. The absorbance is measured at 420 nm. At 30 minutes, one tube containing enzyme is taken out and centrifuged for approximately 2 minutes. The liquid is then poured into a marked tube and 500 μl of the solution is pipetted into another marked tube. To this tube, 700 μl of 0.2M sodium carbonate solution is added to stop the reaction. At 45 minutes, the last two tubes (one tube containing enzyme, the other a control) are taken out and the procedure cited for the 15 minute tubes is repeated.

The U/mg is calculated using the absorptivity of $1.38 \times 10^4 \, M^{-1} \, cm^{-1}$ for $p$-nitrophenol at 420 nm. The absorbance ($A^{1\%}$) of 25.2 for $\alpha$-amylase is also used in calculation of the amount of enzyme present in the assay.

Having thus described the invention, what is claimed is:

1. A process to produce a modified protein from a negative protein comprising the steps of:
   selecting one enzyme to be molded, said enzyme having an enzymatic activity different from said native protein;
   selecting a native protein to be modified to model said enzyme;
   admixing said native protein with a denaturing agent for a time at a temperature sufficient to partially denature said native protein so as to perturb the shape or conformation of said native protein without causing an irreversible, gross denaturation;
   admixing the resulting partially denatured native protein with a competitive inhibitor of said model enzyme; and
   admixing said partially denatured native protein and said inhibitor with a cross-linking agent for a time and at a temperature sufficient to cross-link said partially denatured native protein by forming covalent bonds between reactive sites on said partially denatured native protein in the presence of said inhibitor and produce a modified protein having the biological activity of said model enzyme.

2. The process of claim 1 wherein said native protein is partially denatured by forming an aqueous solution of said native protein and maintaining said aqueous solution at a temperature and for a time sufficiently to partially denature said native protein.

3. The process of claim 2 wherein said time is about 15 minutes to 24 hours and said temperature is about 25° C. to 60° C.

4. The process of claim 1 wherein said native protein is partially denatured by admixing said native protein with water to form an aqueous solution and admixing the resulting solution with a denaturing agent.

5. The process of claim 1 wherein said denaturing agent is an inorganic acid.

6. The process of claim 4 wherein said denaturing agent is an organic acid.

7. The process of claim 4 wherein said denaturing agent is a water-miscible organic solvent.

8. The process of claim 4 wherein said denaturing agent is an inorganic salt.

9. The product of the process of claim 1.

* * * * *